United States Patent [19]
Marsili et al.

[11] 4,086,225
[45] Apr. 25, 1978

[54] RIFAMYCIN COMPOUNDS

[75] Inventors: Leonardo Marsili; Vittorio Rossetti; Carmine Pasqualucci, all of Milan, Italy

[73] Assignee: Archifar Industrie Chimiche del Trentino S.p.A., Rovereto, Italy

[21] Appl. No.: 694,589

[22] Filed: Jun. 10, 1976

[30] Foreign Application Priority Data

Jun. 13, 1975 Italy .................................. 5174A/75

[51] Int. Cl.$^2$ .......................................... C07D 498/18
[52] U.S. Cl. ............................ 260/239.3 P; 424/273 R
[58] Field of Search ................................. 260/239.3 P

[56] References Cited

U.S. PATENT DOCUMENTS 3,338,888  8/1967  Bickel et al. .................. 260/239.3 P

*Primary Examiner*—Natalie Trousof
*Assistant Examiner*—Robert T. Bond
*Attorney, Agent, or Firm*—Oblon, Fisher, Spivak, McClelland & Maier

[57] ABSTRACT

Oxidized rifamycin compounds having high antibiotic activity as obtained by reacting 3-amino-4-deoxo-4-imino-3-rifamycin S or homologous thereof with a ketone.

5 Claims, No Drawings

RIFAMYCIN COMPOUNDS

This invention relates to novel rifamycin compounds having high antibiotic activity. Such compounds are selected from the group consisting of the compounds having the following formula:

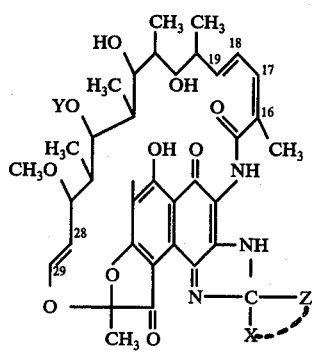

wherein: X is an alkyl having less than 5 C atoms; Y is —H or —COCH$_3$; Z is selected from the group consisting of alkyl with less than 5 C atoms, alkoxy-alkyl with less than 6 C atoms, hydroxyalkyl with less than 4 C atoms, carboxyalkyl with less than 5 C atoms, carbalkoxyalkyl with less than 6 C atoms, halogen-alkyl with less than 4 C atoms, N,N-dialkylaminoalkyl, arylalkyl with less than 10 C atoms, cycloalkyl, and X and Z along with the C atom to which they are bonded form a ring selected from the group consisting of a ring with less than 7 C atoms, a ring with less than 7 C atoms substituted with at least one radical selected from the group consisting of alkyl with less than 4 C atoms, halogen and carbalkoxy, a heterocyclic ring with less than 7 atoms containing one N atom, a heterocyclic ring with less than 7 atoms containing one N atom and substituted with a radical selected from the group comprising alkyl with less than 4 C atoms, arylalkyl with less than 9 C atoms, carbalkoxy and acyl with less than 5 C atoms, and 16, 17, 18, 19-tetrahydroderivatives and 16, 17, 18, 19, 28, 29-hexahydroderivatives thereof.

Rifamycin compounds according to the present invention have high antibacterial activity, particularly on Mycobacterium Tuberculosis. Such compounds are in the form of powders from pink to violet colour, are soluble in most organic solvents and most are water insoluble.

Such rifamycin compounds are obtained by a method wherein a rifamycin compound having the formula

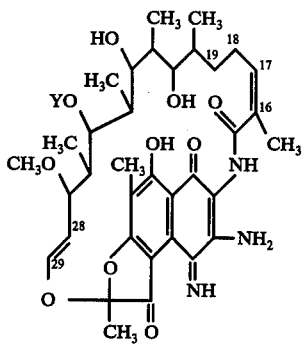

wherein Y is —H or —COCH$_3$; its 16, 17, 18, 19-tetrahydroderivatives and 16, 17, 18, 19, 28, 29-hexahydroderivatives, is reacted with a ketone having the formula

wherein X and Z are those as above defined, and X and Z along with CO form a ring selected from the group consisting of a ring with less than 7 C atoms, a ring with less than 7 C atoms substituted with at least one radical selected from the group comprising alkyl with less than 4 C atoms, halogen and carbalkoxy, a heterocyclic ring with less than 7 atoms containing one N atom, a heterocyclic ring with less than 7 atoms containing one N atom and substituted with a radical selected from the group consisting of alkyl with less than 4 C atoms, arylalkyl with less than 9 C atoms, carbalkoxy and acyl with less than 5 C atoms.

The compound of formula (II) and methods of preparing the same are disclosed in applicants' copending patent application Ser. No. 680,771 filed Apr. 27, 1976.

It has been found that the reaction of ketone of formula (III) with the compound of formula (II) is more readily carried out and with improved yields when such a reaction is effected in the presence of acetic acid and a reducing agent selected from the group consisting of zinc and iron.

In order that the present invention be more clearly understood, some unrestrictive examples thereof will now be shown.

EXAMPLE 1

10 g 3-amino-4-deoxo-4-imino-rifamycin S were dissolved in 20 ml cyclohexanone. The solution was added with 1 g zinc, 20 ml acetic acid and stirred for 60 minutes at room temperature. Unreacted zinc was filtered, and the reaction solution was added with 100 ml dichloromethane, washed with water, dried on sodium sulphate and evaporated to dryness. The residue was dissolved again with 30 ml dichloromethane, the solution added with 200 ml petroleum ether, the precipitate obtained was filtered, then concentrating to 50 ml. 4.8 g were crystallized of a product of formula (I), wherein Y is —COCH$_3$ and X and Z, along with the C atom to which they are bonded, form a cyclohexylidene radical. The chemical-physical characteristics of the product are as follows:

the electronic absorption spectrum in methanol shows peaks at 495, 315 and 275 nm;

I.R. spectrum in nujol shows absorption bands in the region about 3250, and then at 1725, 1665, 1600, 1560, 1515, 1295, 1250, 1175–1155, 1060, 970, 920, 890, 765 and 725 cm$^{-1}$;

nuclear magnetic resonance spectrum in deuterated chloroform, using tetrametylsilane as internal standard, shows the most significant peaks at $\theta$: 0.60(d); 0.83(d); 1.05(d); 3.10(s); 4.81(dd); 5.15(dd); 8.23(s); 9.20(s) and 14.75(s) p.p;m. Also the disappearance of the last three said peaks, when in presence of deuterated water is characteristic.

EXAMPLE 2

10 g 3-amino-4-deoxo-4-imino-rifamycin S were dissolved in 25 ml methylisobutylketone. The solution was added with 1 g zinc, 30 ml acetic acid and heated at 40° C for 30 minutes. Excess zinc was filtered, the reaction solution was added with 100 ml dichloromethane and washed with water. After drying on sodium sulphate and concentration to 20 ml, 100 ml cyclohexane and 50 ml petroleum ether were added. The solution was filtered and the filtered solution was evaporated to dryness.

Yield: 4.4 g product of formula (I), where in Y is —COOH$_3$, X is methyl and Z is isobutyl, with the following chemical-physical characteristics:

the electronic absorption spectrum in methanol shows peaks at 500, 310 and 275 nm;

I.R. spectrum in nujol shows the most significant peaks at: 3400 (sh), 3250, 1725, 1620, 1600, 1560, 1510, 1415, 1290, 1250, 1155, 1060, 970, 945, 915, 890, 810 and 720 cm$^{-1}$.

EXAMPLE 3

8 g 3-amino-4-deoxo-4-imino-rifamycin S were mixed with 2.5 g iron and dissolved in 15 ml acetone and 15 ml acetic acid. After stirring at 35° C for 15 minutes, excess iron was filtered and the solution poured into 600 ml water. The solution was filtered, washed with water, the aqueous phase extracted with toluene after correcting pH to 7 with bisodic phosphate. Toluene was concentrated to 20 ml and then diluted with 80 ml cyclohexane. After filtering, the mixture of the two solvents was evaporated, obtaining 3.5 g product of formula (I), wherein Y is 13 COCH$_3$, Z and X are methyl, and with the following chemical-physical characteristics:

the electronic absorption spectrum in methanol shows peaks at 490, 350(sh), 315 and 270 nm;

I.R. spectrum in nujol shows the most significant peaks at: 3400 (sh), 3250, 1730, 1675, 1650(sh), 1605, 1565, 1515, 1420, 1300, 1250, 1170, 1085, 1065, 975, 950, 930, 895, 815 and 690 cm$^{-1}$.

EXAMPLE 4

8 g 3-amino-4-deoxo-4-imino-rifamycin S were dissolved in 25 ml dioxane, added with 6 g 1-methyl-4-piperidone dissolved in 5 ml dioxane and heated at 70° C for 10 minutes. The solution was poured into 400 ml water containing 20 g sodium chloride, the precipitate filtered, the filtrate extracted with chloroform, the organic phase dried on sodium sulphate and the solvent evaporated. The residue obtained was dissolved in benzene and the solution extracted with an aqueous solution of bisodic phosphate. Benzene was washed with water, the solution dried on sodium sulphate and then evaporated to dryness. Yield: 2.2 g product of formula (I), wherein Y is —COCH$_3$, and X and Z, along with the C atom to which they are bonded, form a 4-(1-methyl) piperidinylidene radical. The chemical-physical characteristics of the product are as follows:

The electronic absorption spectrum in methanol shows peaks at 485, 350(sh), 310 and 270 nm;

I.R. spectrum in nujol shows the most significant peaks at: 3400(sh), 3250, 1730, 1670, 1650(sh), 1605, 1565, 1515, 1420, 1300, 1255, 1180, 1160, 1065, 1015, 975, 950(sh), 920, 895, 815, 770 and 695 cm$^{-1}$;

nuclear magnetic resonance spectrum in deuterated chloroform, using tetramethylsilane as internal standard shows the most significant peaks at $\theta$: -0.16(d); 0.60(d); 0.86(d); 1.04(d); 1.77(s); 2.02(s); 2.06(s); 2.32(s); 2.49(s); 3.10(s); 4.82(d); 5.14(dd); 5.70-6.60(m); 7.0-7.4(m); 8.27(s); 8.97(s) and 14.67(s) p.p.m.

Also the disappearance of the last three said peaks, when in the presence of deuterated water, is characteristic.

EXAMPLE 5

8 g 3-amino-4-deoxo-4-imino-rifamycin S were reacted with 1 g zinc, 15 ml tetrahydrofuran, 8.5 ml 1-carbethoxy-4-piperidone and 25 ml acetic acid at 50° C for 10 minutes. The reaction mixture was filtered and diluted with 200 ml xylene, washed with a phosphate buffer sulution at pH 7.5, then with water and finally dried on sodium sulphate. Xylene was then evaporated to obtain 100 ml solution, which was diluted with 150 ml petroleum ether, filtered and evaporated to dryness. The residue obtained was added again with petroleum ether, diltered and dried. Yield: 5 g product of formula (I), wherein Y is —COCH$_3$ and X and Z, along with the C atom to which they are bonded, form a 4-(1-carbethoxy)-piperidinylidene radical.

The electronic absorption spectrum in methanol shows peaks at 500, 360(sh), 312 and 275 nm.

EXAMPLE 6

8 g 3-amino-4-deoxo-4-imino-rifamycin S were reacted with 1 g zinc, 10 ml tetrahydrofuran, 12 ml chloroacetone and 25 ml acetic acid. After 5 minutes at 60° C, the reaction was completed and after filtering unreacted zinc, the solution was poured into 800 ml buffered solution at pH 7.5 and containing 5 g ascorbic acid. The precipitate obtained was filtered, washed with water and vacuum dried at 40° C. Finally, the residue was continuously extracted with petroleum ether and by solvent evaporation 3.6 g product of formula (I) are obtained, wherein Y is —COCH$_3$, X is methyl and Z is chloromethyl.

The electronic absorption spectrum in methanol shows peaks at 495, 270, 238 and 210 nm.

EXAMPLE 7

8 g 3-amino-4-deoxo-4-imino-rifamycin S were reacted with 1 g zinc, 15 ml tetrahydrofuran, 8 ml 1-benzyl-4-piperidone and 30 ml acetic acid. After stirring at 60° C for 15 minutes, unreacted zinc was filtered, then adding 1 g ascorbic acid, diluting with 300 ml xylene and washing with phosphate buffer solution at pH 7.5 and then with water. After drying the solution on sodium sulphate, the solvent was evaporated to dried residue, which was then continuously extracted with petroleum ether.

After solvent evaporation, 2.5 g product of formula (I) were then obtained, wherein Y is —COCH$_3$, and X and Z, along with the C atom to which they are bonded, for a 4-(1-benzyl)piperidinylidene radical.

The electronic absorption spectrum in methanol shows peaks at 500, 315 and 275 nm.

EXAMPLE 8

8 g 3-amino-4-deoxo-4-imino-16, 17, 18, 19-tetrahydrorifamycin S were reacted with 1 g zinc, 15 ml tetrahydrofuran, 6 ml diethylaminoacetone and 30 ml acetic acid. After stirring at room temperature for 15 minutes, excess zinc was filtered, adding 1 g ascorbic acid and dropwise pouring the solution into 700 ml water.

The precipitate obtained was filtered and dissolved again in minimum volume of methyl alcohol. The methanol solution was diluted with 250 ml ethyl ether and then extracted with phosphate buffer solution at pH 7.5. The aqueous layer was acidified to pH 3 and then extracted with chloroform. The chloroform layer was washed with water, dried on sodium sulphate and evaporated to dryness. Thus, 0.8 g were obtained of 16, 17, 18, 19-tetrahydroderivative of a product of formula (I), wherein Y is —COCH$_3$, X is methyl and Z is diethylaminomethyl.

The electronic absorption spectrum in methanol shows peaks at 455 and 320 nm.

EXAMPLE 9

8 g 3-amino-4-deoxo-4-imino-16, 17, 18, 19, 28, 29-hexahydro-25-desacetyl-rifamycin S were reacted with 1 g zinc, 15 ml tetrahydrofuran, 4.5 g 1-acetyl-4-piperidone and 25 ml acetic acid. After stirring at room temperature for 30 minutes, unreacted zinc was filtered, adding 1 g ascorbic acid and diluting with 300 ml ethyl ether. The ether solution was thoroughly washed with water and then dried on sodium sulphate. Then, the residue was diluted with 50 ml petroleum ether, filtered and evaporated to dryness. 1.7 g 16, 17, 18, 19, 28, 29-hexahydroderivative of a product of formula (I) were obtained, wherein Y is —H and X and Z, along with the C atom to which they are bonded, form a 4-(1-acetyl)-piperindinylidene radical.

The electronic absorption spectrum in methanol shows peaks at 495, 315 and 275 nm.

EXAMPLE 10

8 g 3-amino-4-deoxo-4-imino-rifamycin S were reacted with 1 g zinc, 15 ml tetrahydrofuran, 2.5 g methylcyclopropylketone and 25 ml acetic acid. After 30 minutes at 50° C, unreacted zinc was filtered, the solution was diluted with 100 ml benzene and 300 ml ethyl ether and then washed with phosphate buffer solution at pH 7.5 and finally with water. The organic layer was evaporated, the residue reacted again with 30 ml methyl alcohol and after addition of 5 ml water containing 1 g sodium ascorbate, the solution was dropwise poured into 300 ml saturated aqueous solution of sodium metabisulphite. The precipitate obtained was filtered, washed with water and dried. 2.2 g product of formula (I) were obtained, wherein Y is —COCH$_3$, X is methyl and Z is cyclopropyl.

The electronic absorption spectrum in methanol shows peaks at 500 and 320 nm.

EXAMPLE 11

8 g 3-amino-4-deoxo-4-imino-rifamycin S dissolved in 25 ml tetrahydrofuran were dropwise added to a mixture comprising 1 g zinc, and 5 g 4-phenyl-butan-2-one preheated at 60° C. After stirring at 60° C for 30 minutes, unreacted zinc was filtered, the mixture was added with 1 g ascorbic acid and diluted with 250 ml benzene. The mixture was then thoroughly washed with water, dried on sodium sulphate and benzene evaporated.

The residue obtained was dissolved in minum volume of methyl alcohol, the solution was treated with 5 ml water containing 1 g sodium ascorbate and then poured into 1000 ml water. The precipitate obtained was filtered, washed with water and dried. The product was dissolved again in 40 ml benzene, added with 80 ml petroleum ether, filtered and the solution was evaporated. The residue obtained of violet colour was added with water and filtrate. After drying, 2.8 g product of formula (I) were obtained, wherein Y is —COCH$_3$, X is methyl and Z is β-phenethyl. The electronic absorption spectrum in methanol shows peaks at 500 and 315 nm.

What we claim is:

1. A rifamycin compound having the formula

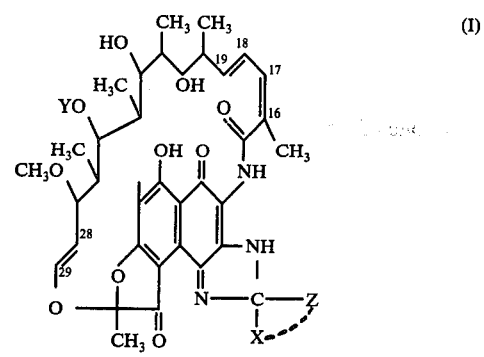

wherein X is alkyl having less than 5 carbon atoms; Y is —H or —COCH$_3$; Z is selected from the group consisting of alkyl having less than 5 carbon atoms, alkoxyalkyl having less than 6 carbon atoms, hydroxy-alkyl having less than 4 carbon atoms, carboxy-alkyl having less than 5 carbon atoms, carbalkoxy-alkyl having less than 6 carbon atoms, halogenalkyl having less than 4 carbon atoms, N,N-dialkylaminoalkyl having less than 6 carbon atoms, aryl hydrocarbon-alkyl having less than 10 carbon atoms and cycloalkyl having less than 7 carbon atoms; or X and Z, along with the C atom to which they are bonded, form cyclic moiety selected from the group consisting of a hydrocarbon ring having less than 7 carbon atoms; a hydrocarbon ring having less than 7 carbon atoms which is substituted with at least one radical selected from the group consisting of alkyl having less than 4 carbon atoms, halogen and carbalkoxy having less than 4 carbon atoms; the piperidine ring; and the piperidine ring which is substituted with a radical selected from the group consisting of alkyl having less than 4 carbon atoms, aryl hydrocarbon-alkyl having less than 9 carbon atoms, carbalkoxy having less than 4 carbon atoms and alkanoyl having less than 5 carbon atoms;

16, 17, 18, 19-tetrahydroderivatives thereof; and
16, 17, 18, 19, 28, 29-hexahydroderivatives thereof.

2. A method of preparing a rifamycin compound of claim 1, which comprises reacting a compound having the formula

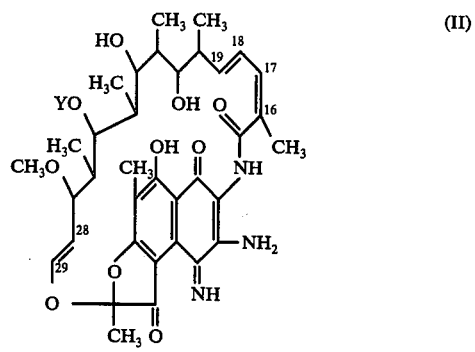

wherein Y is —H or —COCH$_3$, its 16, 17, 18, 19-tetrahydroderivatives or its 16, 17, 18, 19, 28 29-hexahydroderivatives, with a ketone having the formula

wherein X and Z are as defined in claim 1 or X and Z along with the C atom to which they are bonded are as defined in claim 1.

3. The method of claim 2, wherein said reaction with the ketone of formula (III) is carried out in the presence of acetic acid and a reducing agent selected from the group consisting of zinc and iron.

4. A rifamycin compound of claim 1 wherein said cyclic moiety contains the piperidine ring.

5. A rifamycin compound of claim 1 wherein said hydrocarbon ring is the cyclohexane ring.

* * * * *